US00PP30484P2

(12) United States Plant Patent
Van Swieten

(10) Patent No.: US PP30,484 P2
(45) Date of Patent: May 7, 2019

(54) ***PHALAENOPSIS* ORCHID PLANT NAMED 'PHALFYTBE'**

(50) Latin Name: ***Phalaenopsis* hybrid**
Varietal Denomination: PHALFYTBE

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,589

(22) Filed: Mar. 19, 2018

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFYTBE', particularly characterized by having large white flowers with a light yellow-green lip, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFYTBE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFYTBE'.

The new *Phalaenopsis* plant is a product of a planned breeding program conducted by the inventor in Bleiswijk, The Netherlands. The objective of this breeding program was to create a new *Phalaenopsis* plant with large white flowers with a light yellow-green lip, suitable for potted plant production.

The new *Phalaenopsis* plant 'PHALFYTBE' is a result of cross-pollination made by the inventor in April 2008 in Bleiswijk, The Netherlands of the proprietary female, or seed parent, *Phalaenopsis* hybrid '6133-04' (unpatented) with the proprietary male, or pollen parent, *Phalaenopsis* hybrid '01-1988' (unpatented).

The new *Phalaenopsis* was selected by the inventor as a single plant within the progeny of the stated cross-pollination in a controlled greenhouse in Bleiswijk, The Netherlands in November 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017. 'PHALFYTBE' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFYTBE' as a new and distinct variety of *Phalaenopsis* plant.

1) Large white flowers with a light yellow-green lip;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in February 2018. Colors in the photographs may differ from the color values cited in the detailed botanical description, which accurately describe the actual colors of the new variety.

DESCRIPTION OF THE NEW VARIETY

Figure 1:
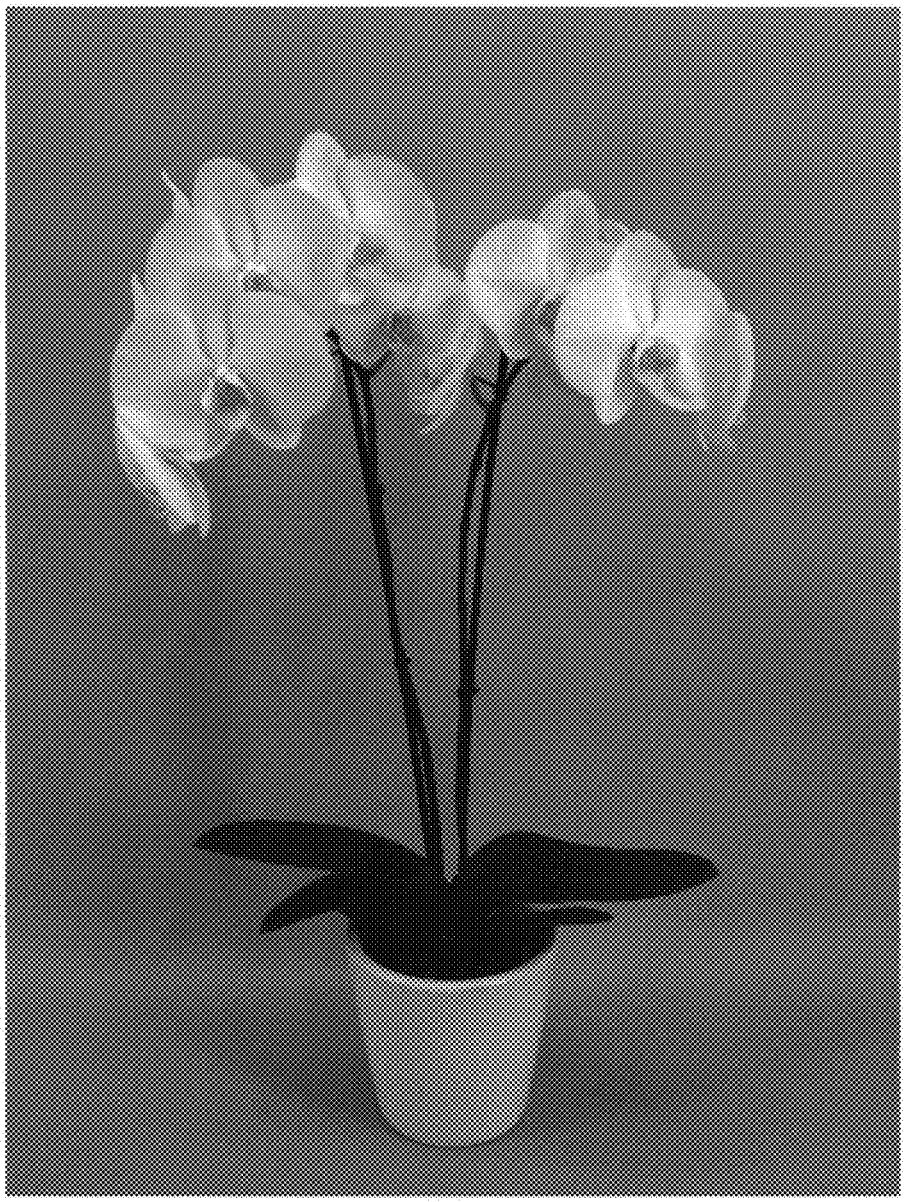
FIG. 1 shows the overall plant habit, including blooms and foliage of 'PHALFYTBE'.
Figure 2:
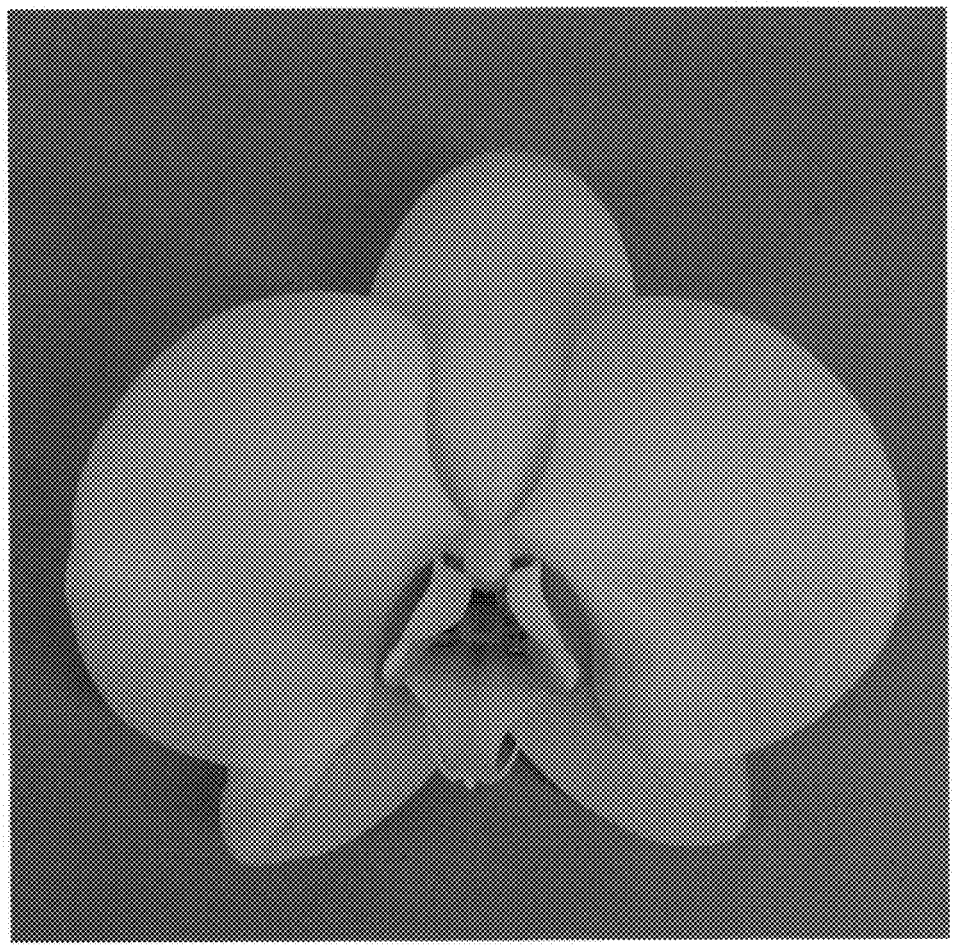
FIG. 2 shows a close-up of a flower of 'PHALFYTBE'.
Figure 3:
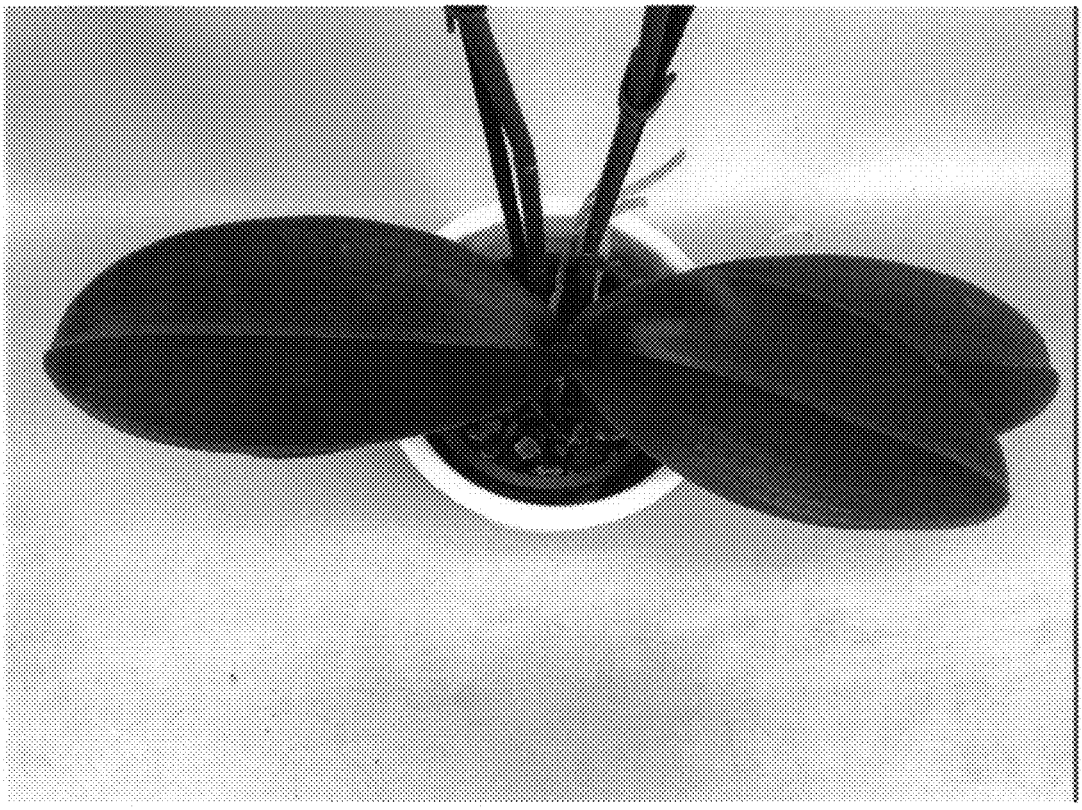
FIG. 3 shows an overhead view of the leaves of 'PHALFYTBE'.

The following detailed description sets forth the distinctive characteristics of 'PHALFYTBE'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in February 2017 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50-weeks in a 12 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFYTBE'.

Parentage:

*Female parent*.—*Phalaenopsis* cultivar '6133-04' (unpatented).

*Male parent*.—*Phalaenopsis* cultivar '01-1988' (unpatented).

Propagation:

*Type*.—Meristem tissue culture.

Roots:

*Root description*.—Greyed-green colored roots (RHS 190B/C) with branching lateral roots having light green (RHS 144C) colored root tips.

Plant:

*Commercial crop time to flowering*.—Following asexual propagation (in-vitro), the rooted cuttings grow for 20-24 weeks. After transplantation in 12 cm pots, the plants are finished after 48 to 50 weeks.

*Growth habit of peduncle*.—Standard, green leaves, raceme to panicle.

*Height* (*from soil level to top of inflorescence*).—Approximately 52.0 cm to 57.0 cm.

*Width* (*measured from leaf tips*).—About 34.0 cm to 36.0 cm.

*Vigor*.—Strong.

Leaves:

*Mature leaves*.—Quantity per plant: 6 to 9 leaves are produced before flowering. Length (fully expanded): 15.0 cm to 18.0 cm. Width: 8.0 cm to 9.0 cm. Shape: Oblong. Base shape: Moderately elongated. Apex: Obtuse unequal. Leaf blade angle with the petiole (measured from the horizontal position): Between 30 degrees and 40 degrees. Leaf margin: Entire. Color: Upper surface: RHS 147A. Lower surface: RHS 147B. Texture: Rough upper surface. Thickness: 2.5 mm to 2.9 mm. Venation: Pattern: Parallel. Color of the midvein: Upper surface: RHS 147A. Lower surface: RHS 147B.

Peduncle:

*Quantity per plant*.—1 to 2.

*Number of flowers per peduncle*.—6 to 10.

*Length*.—52.0 cm to 57.0 cm.

*Diameter*.—5.8 mm to 6.3 mm.

*Strength*.—Strong.

*Aspect*.—Upright to slightly pendant.

*Texture*.—Smooth.

*Color*.—Mix of brown (RHS 200A) and green (RHS 146A).

*Internode length*.—3.0 cm to 4.0 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 200.0 mm to 220.0 mm.

*Flowering time*.—First flowers can be expected 10 to 11 months after planting in a 12 cm (diameter) pot.

*Flower*.—Height: 100.0 mm to 105.0 mm. Diameter: 110.0 mm to 115.0 mm. Depth of lip: 25.0 mm to 27.0 mm.

*Flower longevity*.—On the plant: 13 to 16 weeks.

*Fragrance*.—Absent.

*Flower bud*.—Average size: Large. Length: 24.0 mm to 26.0 mm. Width: 20.0 mm to 22.0 mm. Shape: Egg shaped. Color: Light yellow-green (RHS 145C) with light red-purple shade (RHS 64A).

*Petals*.—Arrangement: Open/free. Shape: Semi-circular. Apex: Rounded asymmetric. Margin: Slightly undulated. Length (from base to tip): 52.0 mm to 54.0 mm. Width: 68.0 mm to 70.0 mm. Color (when fully opened): Upper surface: Basic color: White (RHS NN155C). Over color: Absent. Lower surface: Basic color: White (RHS NN155C). Over color: Absent.

*Dorsal sepal*.—Shape: Elliptic broad. Apex: Emarginated. Margin: Entire. Length (from base to tip): 55.0 mm to 57.0 mm. Width: 40.0 mm to 42.0 mm. Color (when fully opened): Upper surface: Basic color: White (RHS NN155C). Over color: Absent. Lower surface: Basic color: White (RHS NN155C). Over color: Slightly light purple (RHS 76C) in the middle.

*Lateral sepals*.—Shape: Ovate. Apex: Obtuse asymmetric. Margin: Entire. Length (from base to tip): 56.0 mm to 58.0 mm. Width: 31.0 mm to 33.0 mm. Color (when fully opened): Upper surface: Basic color: White (RHS NN155C). Over color: Light green (RHS 145C) at the base. Lower surface: Basic color: White (RHS NN155C). Over color: Light green (RHS 145C) at the base and slightly light purple (RHS 76C) at the apex.

*Labellum* (*lip*).—Whiskers: Present. Length of whiskers: 34.0 mm to 36.0 mm. Color of whiskers: White (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 22.0 mm to 24.0 mm. Width: 18.0 mm to 20.0 mm. Color: Yellow-green (RHS 151D) at the base and few red-brown (RHS 174A) stripes; white (RHS NN155C) toward the margin.

*Apical lobe*.—Shape: Triangular. Margin: Entire. Length: 21.0 mm to 23.0 mm. Width: 25.0 mm to 27.0 mm. Color: Yellow-green (RHS N144A) at the base and red-brown (RHS 174A) edge toward the callus; white (RHS NN155C) toward whiskers.

*Callus*.—Average size: Medium. Height: 0.6 cm to 0.7 cm. Length: 0.6 cm to 0.7 cm. Width: 0.5 cm to 0.6 cm. Color: Yellow (RHS 6A) with red-brown (RHS 174A) dots.

Reproductive organs:

*Column*.—Length: 9.0 mm to 11.0 mm. Diameter: 6.0 mm to 6.3 mm. Color: White (RHS NN155C).

*Pollinia*.—Quantity: 2. Diameter: 0.9 mm to 1.1 mm. Color: Orange (RHS N25A).

*Ovary*.—Length: 8.0 mm to 10.0 mm. Diameter: 2.5 mm to 2.7 mm.

*Pedicel*.—Length: 37.0 mm to 39.0 mm. Diameter: 2.8 mm to 3.1 mm. Color: Green (RHS 146C) and greenish white (RHS 157D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFYTBE' differs from female parent plant '6133-04' (unpatented) in that 'PHALFYTBE' has white whiskers, a white-green ovary, and red-brown stripes on the apical lobe, whereas '6133-04' has yellow whiskers, a light purple ovary, and red stripes on the apical lobe. Additionally, 'PHALFYTBE' has longer whiskers than '6133-04'.

'PHALFYTBE' differs from male parent plant '01-1988' (unpatented) in that 'PHALFYTBE' has white whiskers, a white-green ovary, and red-brown stripes on the apical lobe, whereas '01-1988' has yellow whiskers, a pinkish white ovary, and red stripes on the apical lobe. Additionally, 'PHALFYTBE' has longer whiskers than '01-1988'.

'PHALFYTBE' is most similar to the commercial *Phalaenopsis* plants named 'PHALFOREI' (U.S. Plant Pat. No. 28,944) and 'PHALDIPWEQ' (U.S. Plant Pat. No. 26,466). 'PHALFYTBE' differs from the commercial variety 'PHALFOREI' in that 'PHALFYTBE' has white whiskers, whereas 'PHALFOREI' has yellow whiskers. Additionally, 'PHALFYTBE' has larger flowers, longer dorsal sepals, and longer whiskers than 'PHALFOREI'.

'PHALFYTBE' differs from the commercial variety 'PHALDIPWEQ' in that 'PHALFYTBE' has white whiskers, whereas 'PHALDIPWEQ' has white whiskers with yellow tips. Additionally, 'PHALFYTBE' has a smaller callus than 'PHALDIPWEQ'.

I claim:

1. A new and distinct variety of *Phalaenopsis* plant named 'PHALFYTBE', substantially as described and illustrated herein.

* * * * *